United States Patent
Eslami et al.

(10) Patent No.: US 8,083,740 B2
(45) Date of Patent: Dec. 27, 2011

(54) DEVICE FOR FACILITATING THE HEALING OF BONE INCLUDING OLECRANAN

(76) Inventors: Maryam Eslami, Tehran (IR); Parvaneh Reshteh Ahmadi, Tehran (IR)

(*) Notice: Subject to any disclaimer, the term of this patent is extended or adjusted under 35 U.S.C. 154(b) by 516 days.

(21) Appl. No.: 12/239,780

(22) Filed: Sep. 28, 2008

(65) Prior Publication Data
US 2010/0076435 A1    Mar. 25, 2010

(51) Int. Cl.
*A61F 5/04* (2006.01)
(52) U.S. Cl. .......................... 606/56; 606/58
(58) Field of Classification Search ............ 606/54, 606/55, 59, 90, 56, 57, 58, 62, 63, 64; 623/21.11, 623/21.12
See application file for complete search history.

(56) References Cited

U.S. PATENT DOCUMENTS

| | | | | |
|---|---|---|---|---|
| 3,985,127 A | * | 10/1976 | Volkov et al. | 606/90 |
| 5,314,426 A | * | 5/1994 | Pohl et al. | 606/58 |
| 5,643,258 A | * | 7/1997 | Robioneck et al. | 606/54 |
| 7,153,302 B1 | * | 12/2006 | Hajianpour | 606/57 |
| 7,169,149 B1 | * | 1/2007 | Hajianpour | 606/54 |
| 2003/0149429 A1 | * | 8/2003 | Ferrante et al. | 606/59 |
| 2005/0043730 A1 | * | 2/2005 | Janowski et al. | 606/56 |
| 2006/0200127 A1 | * | 9/2006 | Ismail | 606/59 |

* cited by examiner

*Primary Examiner* — Eduardo C Robert
*Assistant Examiner* — Atiya Mahmud
(74) *Attorney, Agent, or Firm* — Barry Choobin; Choobin & Choobin Consultancy L.L.C.

(57) ABSTRACT

A Mini External Fixate device is disclosed in closed operations in order to fix fractures of elbow bone especially olecranon and cure its problems including mal-unions and non-unions, correcting elbow deformities, lengthening the bone length up to 5 cm. The device comprises three curved plates which are connected by a threaded rod. The device may further comprise two half pin consuls which go through each curved plate in one direction. The half pin consuls may extend as far as they are connected to the fracture, while they don't reach the other side of the bone. Half pins may be used instead of full pins in this device. The half pin consuls may be attached to the curved plate by means of a wire fixation bolt. A hinge may be attached to the extreme of the threaded rod.

7 Claims, 4 Drawing Sheets

DEVICE FOR FACILITATING THE HEALING OF BONE INCLUDING OLECRANAN

CROSS-REFERENCE TO RELATED APPLICATIONS

This application claims the benefit of Provisional Application No. 60/074,635, filed Jun. 22, 2008.

BACKGROUND OF THE INVENTION

Field of the Invention

The present invention relates to subject matter which provides the joining means between the external fixator structure and an elongated transcutaneous fastener element which is secured in a bone fragment to be fixated, and more particularly relates to treatment of orthopedic fractures, specially to a device for external fixation of bone fractures, in particular fractures of the olecranon, treatment of non-unions, mal-unions, correction of deformities of bones, growing length of the bone up to 5 cm, and stabilizing bone after removing bone tumors form the bone.

Various methods are employed to set a broken bone and to maintain bone fragments in a fixed position during a period of healing. Relative movement of the bone fragments must be prevented during the healing period so that the bone may properly heal. Additionally, it may be desirable to keep the bone fragments under compression during healing, because compression of the bone fragments increases the rate of healing.

A cast, or splinting, is often adequate for fixation of some types of fracture. However, certain bones, or portions of certain bones, are not adequately stabilized or fixated by casting or splinting. Surgical techniques may be employed to place pins, wires, screws, plates, and the like to hold bone fragments in place. Various techniques for placement of the pins, wires, screws, and plates have been devised, and frequently require an open surgical technique to place pins, wires, screws, or plates in fragments of the fractured bone, as well as in adjacent bones in some circumstances. Such open surgical techniques are often more invasive that is desirable. Additionally, further devices that may be employed to hold the pins, wires, screws, or plates stably in place can limit movement of an affected limb.

In certain bones, such as the olecranon, difficulty in treating a fracture is compounded because muscles in connection with the bones, or with fragments of the bones, tend to pull the bone fragments apart along a fracture, rather than compress the fragments together. Moreover, given their proximity and relation to limb joints for example elbow, the treatment of fractures of the olecranon may impact the motility of a patient if such treatment restricts the joint movement.

Treatment of elbow bone depends on how it has been broken. It may include fixation of by consideration the type of fracture includes elbow by means of fixing frames or casting. If a part of the bone is broken away, operation will be needed.

When a certain bone is not fixed enough by casting or fixing frames, the open operation techniques are used to put pins, bolts and wires in their places in order to keep the broken bone in its place.

During the recent century, the usage of external fixators in treatment of bone maladies has been increased due to numerous advantages of such devices. After invention of the first external fixator, scientists have always tried to add up to advantages of such devices to treat patients more quickly and with fewer side effects.

When a certain bone like elbow is casted or fixed by frames, due to existence of attached muscles with this bone or bone particles which tend to separate bone particles along the broken part, and also the limb's especially olecranon proximity with elbow joint in treatment of broken elbow bone, the patient's ability to move is restricted.

Fracture bone of this area will cause side effects such as malunion, nonunion, deformities, shortened bones, reduction of movement span, damage to veins, nerves and tendons and severe infection.

A new device for fixation of fractured bones, such as the olecranon, that allows early movement of elbow joints with full weight bearing following a fracture and treatment, is desirable to promote a swift and full recovery and overcome the above shortcomings.

Thus, a method and device for external fixation of bone fractures solving the aforementioned problems is desired.

SUMMARY OF THE INVENTION

The present invention relates to subject matter which provides the joining means between the external fixator structure and an elongated transcutaneous fastener element which is secured in a bone fragment to be fixated, and more particularly relates to treatment of orthopedic fractures, specially to a method and device for external fixation of bone fractures, especially fractures of the olecranon, treatment of non-unions, mal-unions, correction of deformities of bones, growing length of the bone up to 5 cm, and stabilizing bone after removing bone tumors form the bone.

A primary object of the present invention is to provide a mini external fixator device for curing elbow bone fractures including olecranon.

Another object of the present invention is to provide a method and device to correct elbow deformities.

Yet another object of the present invention is to provide a method and device to increase the length of the bone up to 5 centimeter.

Yet another object of the present invention is to provide a method and device to allow basic movement of the joints by means of half-pin consuls.

Another object of the present invention is to provide a method and device to compress destruction for correcting deformities and deviations of the bone.

Yet another object of the present invention is to provide a method and device to simultaneously treat the bone fractures and the deviation of said bone.

In preferred embodiment, the present invention discloses a device for external fixation of bone fractures including olecranon consisting: a threaded rod wherein said threaded rod comprises, a first end and a second end; at least one curved plate, wherein said at least one curved plate comprises a first aperture, a second aperture and a third aperture, wherein said threaded rod passes through second aperture; at least one pair of pins wherein said at least one pair of pins comprises a first end and a second end, wherein said at least one pair of pins are connected to said each of at least one curved plate by at least one bolt and at least one nut, wherein said first end of at least one pair of pins is inserted to the bone and not projected out of other side of said bone, and said second end of at least one pair of pins is affixed to said at least one curved plate by said at least one bolt and at least one nut; a second pin, wherein said second pin is inserted through said olecranon bone fracture on a proximal side of said olecranon bone fracture, and a distal side of said olecranon bone fracture and not projected out of other side of said bone; means for securing said second pin with said threaded rod by a hinge, a pair of washers, at least a nut and at least a bolt, wherein said threaded rod is inserted into said hinge.

In one embodiment, the present invention discloses a Mini External Fixate device that is used in closed operations in order to fix fractures of elbow bone especially olecranan and cure its problems including mal-unions and non-unions; correcting elbow deformities, lengthening the bone length up to 5 cm and stabilizing bone after removing bone tumors form the bone.

Yet in another embodiment, the device comprises three curved plates which are connected by a threaded rod. The device may comprise further two half pin consuls which go through each curved plate in one-way direction. The half pin consuls may extend as far as they are connected to the fracture, while they don't reach the other side of the bone. Half pins may be used instead of full pins in this device. The half pin consuls may be attached to the curved plate by means of a wire fixation bolt. A hinge may be attached to the extreme of the threaded rod. Then, the long pin consul may pass through the bone so that it goes beyond the broken area and is fixed in the bone. Then the external extreme of the long pin consul may be fixed to the hinge. If there are deviations, fractures, or other problems beyond the broken area, they may be cured simultaneously through adding curved plates and hinges. After installing the device on the related limb, there will be a potential of compress destruction.

In an alternative embodiment, the present invention discloses a method of external fixation of bone fractures, by using the device for fixation of bone fractures, wherein the elbow bone is first put in place and then fixed temporarily. Then the long pin consul is passed through broken parts and is connected to holding part of the device. The device may be fixed by means of half pin consuls and curved plates which allow fixation and compression of bone particles.

In another embodiment of the present invention, the deviation of bones is corrected and the bone is lengthened up to 5 cm in length. Since the pins used are in the form of half pins which do not project out of the bone through the other side of the bone, there is very little possibility that veins, arteries, nerves, tendons, skin and muscles are damaged and infected. Also the use of half pins prevents the veins, arteries, nerves, tendons, skin and muscles from getting damaged and infected. Thus the possibility of infection and pain and other side effects, after operation is reduced in comparison with other methods.

A bone growth process or a bone lengthening process performed using the device disclosed in the embodiments is as follows. After placing the half pins and inhibiting them with curved plate, when the length of the bone is to be extended more, the distance between two pieces of bone is increased by increasing the distance between these rings from each other through the assembly of the screws, so that the two pieces of the bone are distanced from each other by one forth of a millimeter during a day, so the bone is lengthened or grown by one millimeter longer in a day. The average growth caused by this system is in the range of 0.5 mm to 1.5 mm in a day. (In other words about 3 centimeters in a month) and after about 1.5 month, the growth of the bone will be equal to 5 centimeters.

Yet in an alternative embodiment, the present invention discloses, that the curved plates and hinges may be added to the device to extend its length, and treat angle deviation and other problems of the bone. In fact the use of threaded rod joint may lead to treatment of various fractures and correction of bone deviations.

Yet in an alternative embodiment, the present invention discloses a method for treating simultaneously fractures and deviations of the bone.

When this device is used, there will be no need to bone transplantation, as the bone deformaties are corrected, the bone is lengthened and the bone is stabilized after removing the tumor. Further the use of half pins prevents the infection and the damage to the bones.

As this device is lighter in comparison to other devices, its use and carrying is easier for patients.

As the device is light and small in size, therefore it is more advantageous to be used by children, old and weak patients.

In another embodiment of the present invention, in order to correct bone deviations, hinges may be added to the device to correct its angle of deviation. In this method, the patient does not need to be hospitalized and can perform their personal affairs while the device is installed.

Considering that there is no need for cutting the skin or muscles for installing the device due to its small size and simple structure, the patient will feel less pain in comparison with the patient whom their skin or muscles should be cut, while the device is being installed. Rehabilitation rate of the patient using this device is very high and is approximately 1-3 months in average. There is no age limit for using this device. The device will also conquer the need of amputation and planting prosthesis, as the half pin consuls do not project out of the other side of the bones thereby causing less harms on the veins, arteries, nerves, tendons, muscles and skin and prevents infections of the bones. Moreover the half pin consuls and curved plates allow the fixation and the compression of the bone particles so that bone deformities are corrected. There is the ability to place and pass the pins along various ways and routes. Taking various medicine and antibiotics is not needed during treatment period.

The patient does not need to be hospitalized in a hospital or at home, and can continue his studies or job during the treatment period, which prevents material and spiritual damages to the patient.

The device due to its small size and simplicity prevents the need for long term anaesthesia, and especially in patients with respiratory problems whose anaesthesia period is very important. Further local anaesthesia can also be applied for installing the device, when employing open surgical techniques to place pins, wires or plate in fragments of the fractured bone.

The features and advantages of the present invention described above, as well as additional features and advantages, will be readily apparent to those skilled in the art upon reference to the following detailed description and the accompanying drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention is a device for external fixation of bone fractures which is especially suitable for external fixation of elbow broken bones especially the olecranon. The device has other capabilities including treatment of non-unions, mal-unions, correction of deformities, growing length of the bone up to 5 cm, fixation after removing bone tumors except for the areas where there is a great mass of muscles.

Figure 1:
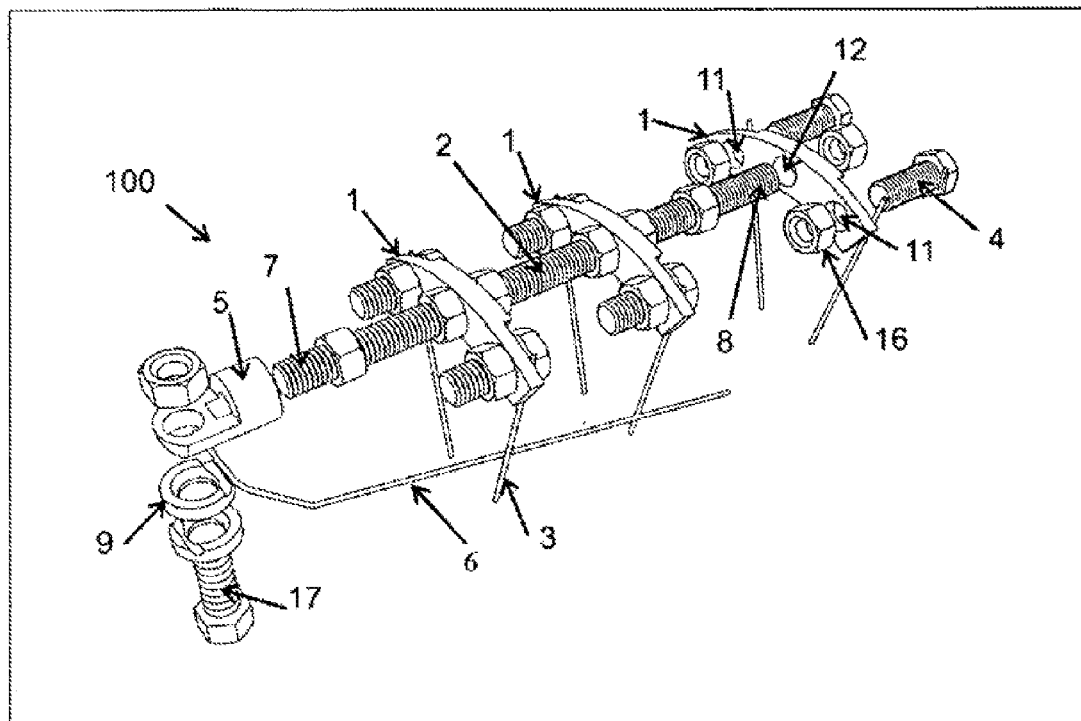
FIG. 1 is a perspective view of one embodiment of an apparatus for external fixation of bone fractures according to the present invention.

Referring now to the drawings wherein like numerals refer to like parts, FIG. 1 illiterates the device (100) which is used for external fixation of bone fractures especially olecranon. The device includes a threaded rod (2) which is an extended bar with a starting end (7) and a finishing end (8).

Three curved plates (1) along the threaded rod are used. The first curved plate part (1) is attached close to the starting end (7) of the threaded rod (2). The third curved plate part (1) is placed in the finishing end (8) of the threaded rod (2).

Middle Curved plate (1) is installed on threaded rod (2) and between both starting and ending curved plates (1). The curved plates (1) are fasten in both sides by wire fixation bolt (4) and nut (16). Curved plates (1) are designed in a way that a number of half pin consuls (3) can be connected to them (1). For this purpose, each curved plate has three holes with diameters relevant with wire fixation bolts. It passes through the middle hole (11) of the threaded rod and also side holes (12) of wire fixation bolt (4). A hinge (5) at the starting end (7) of the threaded rod (2) is used for fixing long pin consul (6) which is connected to each other by a pair of slotted washer (9), a long wire fixation bolt (17) and a nut (16).

Figure 2:
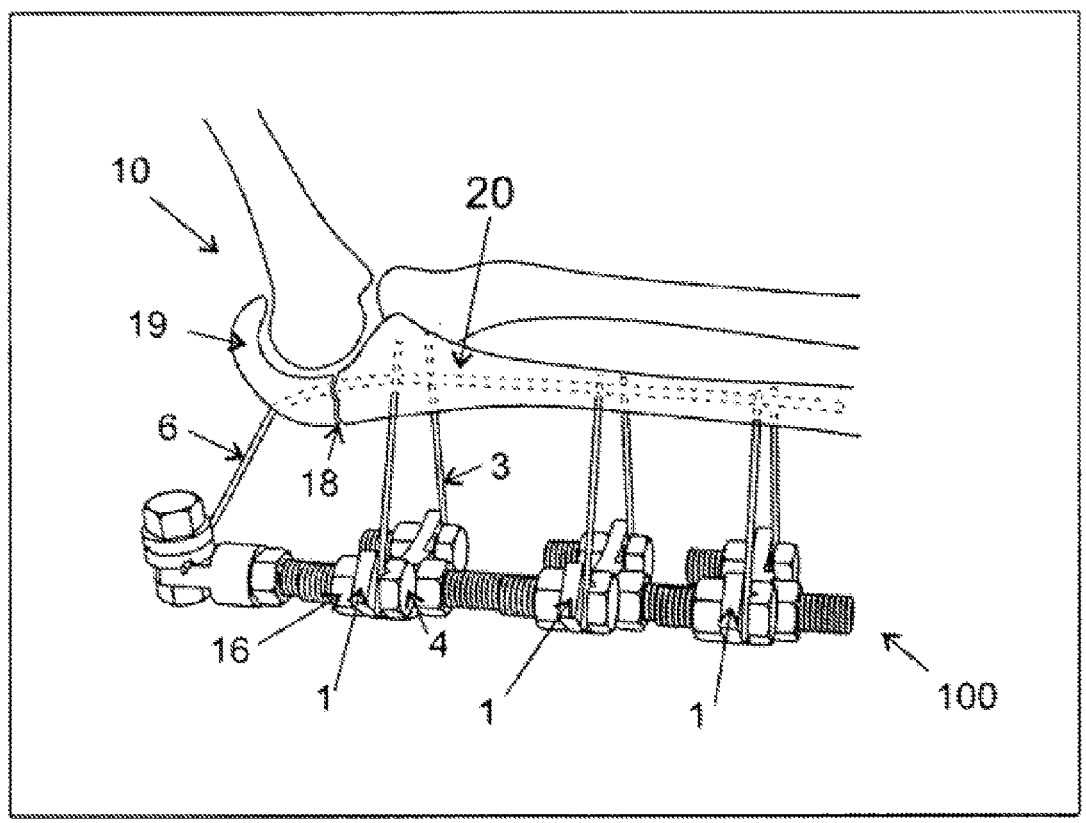
FIG. 2 is an environmental, perspective view of an apparatus for external fixation of bone fractures according to the present invention, placed to fixate a broken elbow bone.

FIG. 2 illustrates External fixation of bone fractures device (100) is used for fixation of a broken elbow bone (10). A fracture line (18) in elbow bone, has divided it into a proximal fragment (19) and a distal fragment (20). Long pin consul (6) is passed through the proximal fragment (19) and distal fragment (20) along the fracture.

Half pin consuls (3) on each side are usually parallel and create an angle of about 45 degrees with the surface of the bone.

On the contrary of other common devices, the important point is that such half pin consuls (3) do not project out of the other side of the bone, thus cause less harms on the veins, arteries, nerves, tendons, muscles and skin.

In order to fix the half pin consuls (3) on the curved plates (1) grooved wire fixation bolts (4) are used. One extreme of half pin consuls (3) will be located in the head groove of wire fixation bolt (4) and is fixed by a nut (16). It is clear that, as discussed before, the other end of half pin consuls (3) are installed on the bone.

The noteworthy point regarding long pin consuls (6) is that relevant to type of elbow fracture; its entrance angle can be modified. In the same way, there is the possibility of creating an angle in half pin consuls (3).

Figure 3:
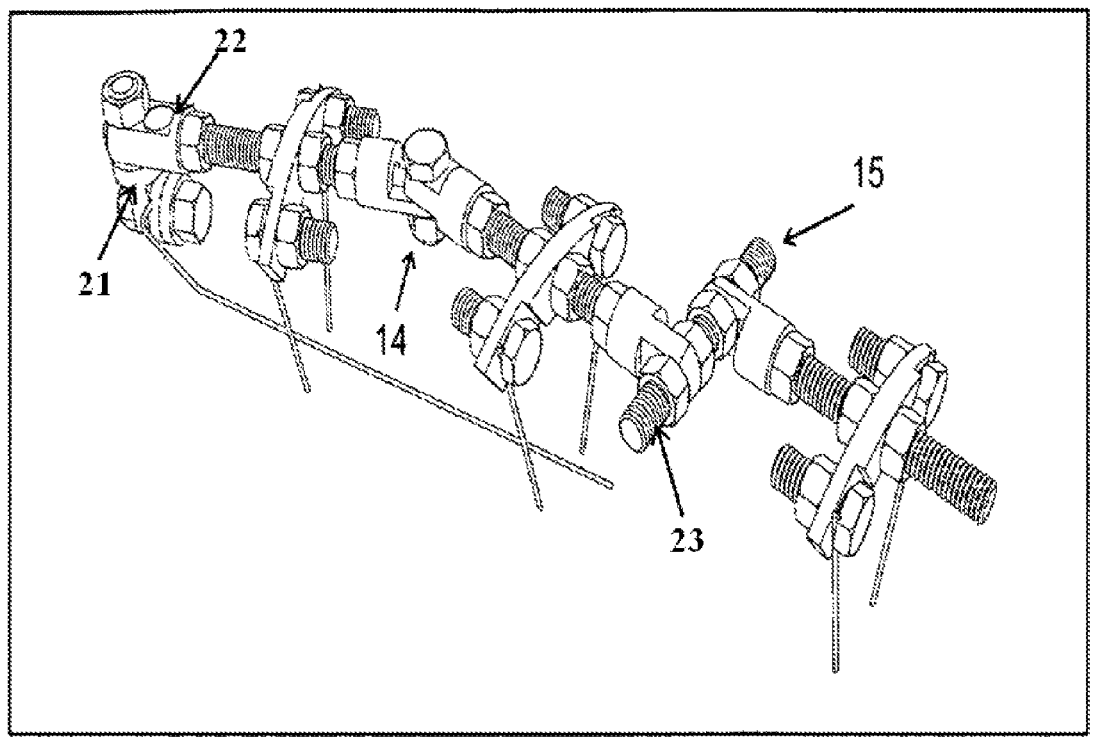
FIG. 3 is a perspective view of another embodiment of an apparatus for external fixation of bone fractures according to the present invention by using hinges for creating a change of angle along with the threaded rod.
Figure 4:
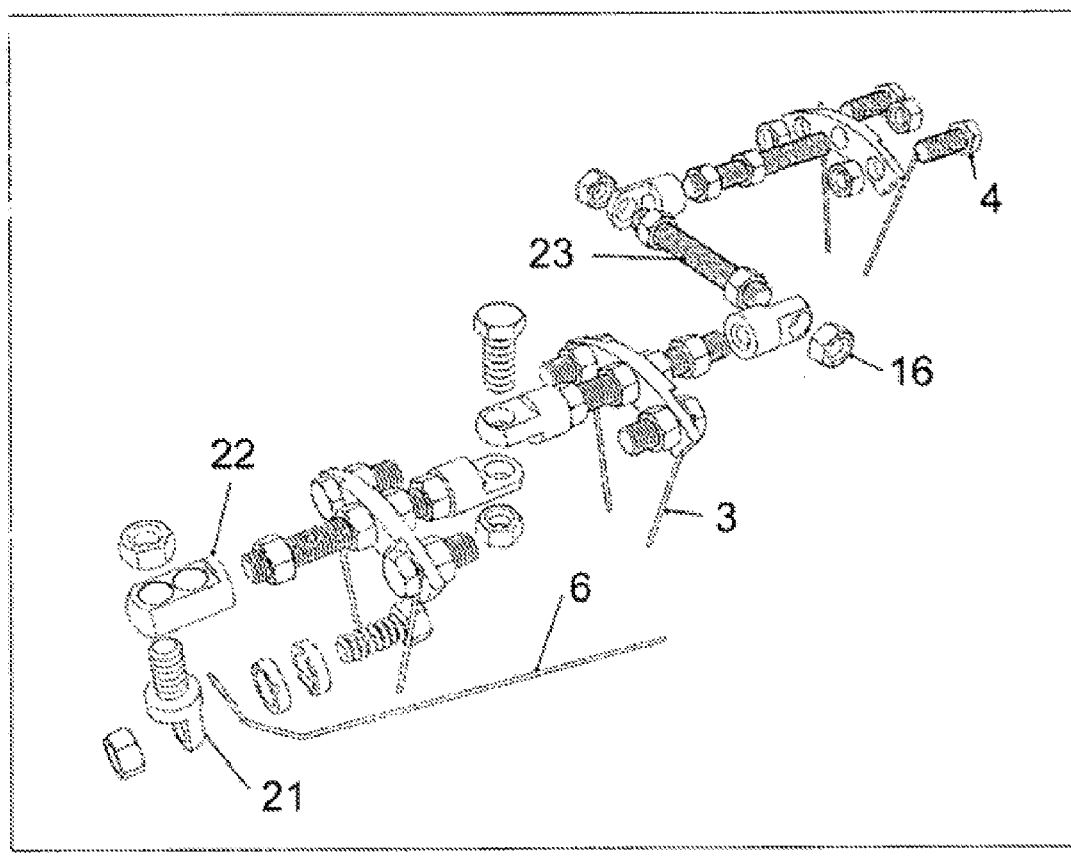
FIG. 4 is a perspective view an apparatus according to the present invention for external fixation of bone fractures allowing an angle of rotation.

As shown in FIG. 3, in cases where the bone is deviated or has changed its angle, by adding hinges (15 and 14), the capabilities of the device can be increased to treat both fracture and deviation at the same time. In this case, the angle of the bone can be modified outside the body by use of compress destruction and using bolts. In fact, the objective of using hinges is creating a change of angle along with the threaded rod.

As shown in FIG. 3, in order to create a hinge, a short threaded rod (23) and two other types of hinges should be used; bolt hinge (21) and double hold hinge (22).

By using these two kinds of hinges, relevant with form of fracture, several types of hinges may be created. For example it is seen in the FIG. 3 that hinge 14 is created along with threaded rod (2), and hinge (15) have allowed a change of angle for the device. In order to connect the two hinges in the area of hinge, a short threaded rod (23) with a wire fixation bolt (4) and one or several nuts (16) may be used.

While more strength of the device is needed inside the bone, a spotted half pin consul may be used instead of an ordinary half pin consul (3). Spots on the surface of the pins allow for better fixation of pins inside the bone.

When the treatment period is over and the bone is reunited and the device is not needed any more, it can be removed out of the patient's body through removing half pin consuls (3) and long pin consuls (6). There will be no operation scars left, which is important considering beauty of the patient. Moreover, it is very important that the possibility of infection is reduced and there will be no need for open surgery.

A patient, due to an accident, faces a disjoint and fractured elbow (olecranon). Due to problems in respiratory system and high risk of operation, no physicians underwent the operation risk. Finally, after installing this device, the elbow problems were treated and no problems occurred since the device has been removed.

Although the invention has been described and illustrated with respect to certain preferred embodiments, it should be understood that the description is for illustration and example only, and is not meant to limit the spirit and scope of this invention.

What is claimed:

1. A device for external fixation of bone fractures, non-unions, and mal-unions including olecranon comprising:

A threaded rod wherein said threaded rod comprises a first end and a second end;

At least one curved plate, wherein said at least one curved plate comprises a first aperture, a second aperture and a third aperture, and wherein said threaded rod passes through said second aperture;

At least one pair of pins wherein said at least one pair of pins comprises a first end and a second end, and wherein said at least one pair of pins are connected to said each of at least one curved plate by at least one bolt and at least one nut, and wherein said first end of said at least one pair of pins is configured to be inserted into a bone and not projected out of an other side of said bone, and said second end of said at least one pair of pins is affixed to said at least one curved plate by said at least one bolt and said at least one nut;

A second pin, wherein said second pin is configured to be inserted through said olecranon bone fracture on a proximal side of said olecranon bone fracture, and a distal side of said olecranon bone fracture and not projected out of other side of said bone, and wherein said second pin is a long pin consul;

Means for securing said second pin with said threaded rod by a hinge, a pair of washers, at least a nut and at least a bolt, wherein said threaded rod is inserted into said hinge;

wherein said at least one pair of pins are half pin consuls; and wherein said device further comprises a means for changing an angle of said half pin consuls along with said threaded rod, wherein said means for changing an angle of said half pin consuls include said at least one hinge into said hinge.

2. The device as claimed in claim 1, wherein said device comprises a means for correcting deformities of said bone, and wherein said means for correcting deformities of said bone is a hinge and wherein said deformities includes fractures and bone deviations and wherein said device treats both said fractures and bone deviations at a same time.

3. The device according to claim 2, wherein said hinge is a bolt hinge and wherein said hinge is a double hold hinge.

4. The device as claimed in claim 1, wherein said device further comprises a means for growing a length of said bone up to 5 cm, wherein said means for growing the lenth of said bone includes said at least one curved plate and said hinge.

5. The device as claimed in claim 1, wherein said half pin consuls are arranged on each side of said bone, and are parallel with respect to each other, thereby creating an angle of about 45 degrees with a surface of said bone.

6. The device as claimed in claim 1, wherein said half pin consuls are a plurality of spotted half pin consul, and wherein spots on a surface of said spotted half pin consul are adapted to allow for a better fixation of said half pin consuls inside said bone.

7. The device as claimed in claim 1, wherein said device stabilizes said bone after removing bone tumors from said bone.

\* \* \* \* \*